(12) United States Patent
Macuch et al.

(10) Patent No.: US 8,561,458 B2
(45) Date of Patent: Oct. 22, 2013

(54) CORROSION RACK AND METHOD OF MONITORING CORROSIVE ELEMENTS

(75) Inventors: Patrick J. Macuch, Naperville, IL (US); Paul B. Desch, Naperville, IL (US)

(73) Assignee: Nalco Company, Naperville, IL (US)

( * ) Notice: Subject to any disclaimer, the term of this patent is extended or adjusted under 35 U.S.C. 154(b) by 299 days.

(21) Appl. No.: 12/142,463

(22) Filed: Jun. 19, 2008

(65) Prior Publication Data
US 2009/0314068 A1 Dec. 24, 2009

(51) Int. Cl.
*G01N 17/00* (2006.01)
(52) U.S. Cl.
USPC .............................. 73/86; 137/268; 248/218.4
(58) Field of Classification Search
USPC .................. 248/274.1, 295.11, 218.4, 219.3, 248/220.21, 229.15, 229.25, 228.6, 230.6, 248/231.71, 241, 243, 244, 245; 211/87.01, 211/94.01; 40/642.02, 654.01, 657; 137/268; 73/86
See application file for complete search history.

(56) References Cited

U.S. PATENT DOCUMENTS

| | | | | |
|---|---|---|---|---|
| 2,437,344 A | * | 3/1948 | Behlmann | 174/163 F |
| 3,717,258 A | * | 2/1973 | McKinnon | 211/87.01 |
| 4,120,313 A | * | 10/1978 | Lewis | 137/268 |
| 4,179,920 A | * | 12/1979 | Schuller et al. | 73/86 |
| 4,488,939 A | | 12/1984 | Fu | |
| 4,697,465 A | * | 10/1987 | Evans et al. | 73/866.5 |
| 4,787,591 A | * | 11/1988 | Villacorta | 248/316.7 |
| 4,869,874 A | | 9/1989 | Falat | |
| 4,903,929 A | * | 2/1990 | Hoffman | 248/229.15 |
| 5,095,977 A | * | 3/1992 | Ford | 166/113 |
| 5,284,063 A | * | 2/1994 | Newell | 73/822 |
| 5,411,890 A | | 5/1995 | Falat | |
| 5,529,272 A | * | 6/1996 | Baublitz, Sr. | 248/231.71 |
| 5,664,750 A | * | 9/1997 | Cohen | 248/231.71 |
| 5,765,791 A | * | 6/1998 | Givonetti | 248/118 |
| 6,209,832 B1 | * | 4/2001 | Yamazaki | 248/230.6 |
| 6,644,483 B1 | * | 11/2003 | Lai | 211/87.01 |
| 6,698,124 B2 | * | 3/2004 | Kump et al. | 40/642.02 |
| 2005/0126269 A1 | | 6/2005 | Souers | |
| 2006/0096360 A1 | | 5/2006 | Bennett | |
| 2007/0120572 A1 | | 5/2007 | Chen et al. | |

* cited by examiner

*Primary Examiner* — Nkeisha Smith
(74) *Attorney, Agent, or Firm* — Edward O. Yonter; Andrew D. Sorensen

(57) ABSTRACT

The current invention relates to a bracket for use in conjunction with test coupons to allow for the consistent and long term monitoring of corrosive elements in a facility. The invention is able to have multiple coupons attached to a single bracket allowing for the testing various corrosive elements. Additionally the coupons can be placed at varying angles and locations to allow for a more complete analysis of the environments.

11 Claims, 3 Drawing Sheets

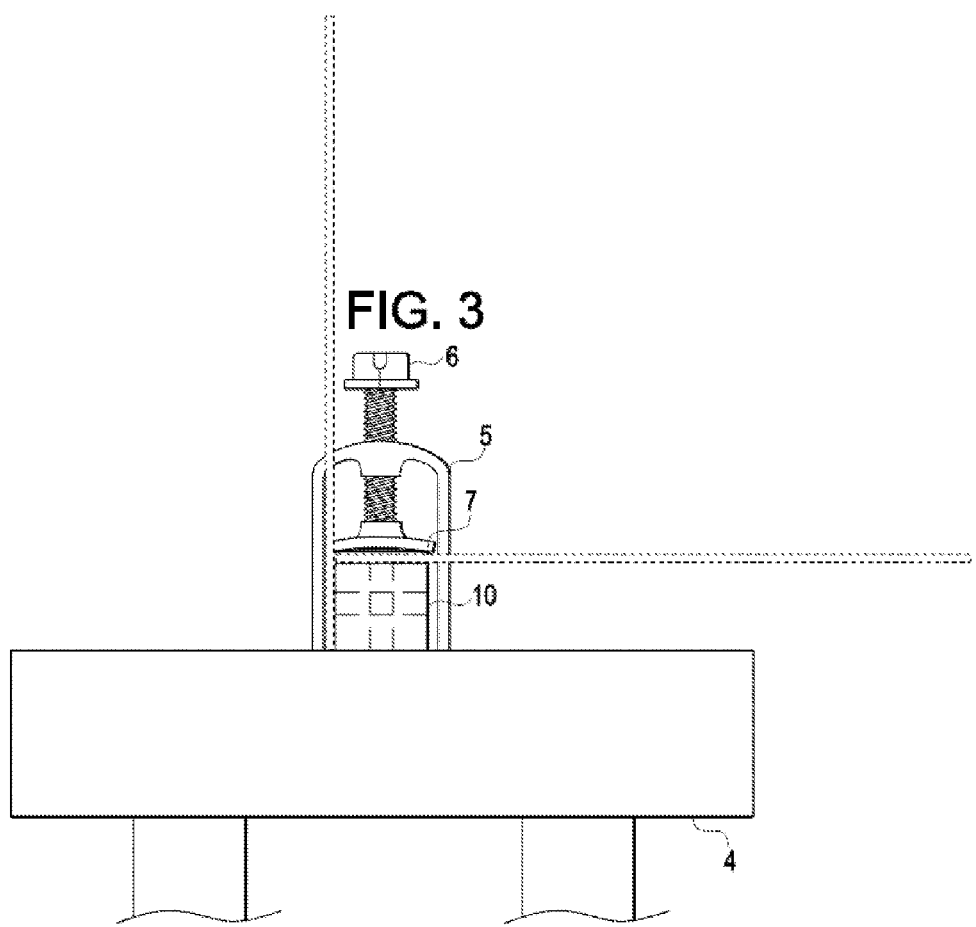

CORROSION RACK AND METHOD OF MONITORING CORROSIVE ELEMENTS

COPYRIGHT NOTICE

A portion of the disclosure of this patent document contains or may contain copyright protected material. The copyright owner has no objection to the photocopy reproduction by anyone of the patent document or the patent disclosure in exactly the form it appears in the Patent and Trademark Office patent file or records, but otherwise reserves all copyright rights whatsoever.

TECHNICAL FIELD

This invention relates to an apparatus that is used to support test coupons that are used to monitor the effects of degradation on various materials in an industrial site. The invention shows the method and the apparatus for consistent and long-term data collection through the use of coupons to assist in the monitoring and adjusting chemistry to reduce degradation of materials in a facility.

BACKGROUND

The invention described here pertains to a rack that is easily integrated into a facility allowing for monitoring the degradation of materials in the environment and better allow industry to address the issues of degradation on materials and equipment. The basis for method of use is that the current invention allows for the consistent placement of the corrosion coupons at the same level and location to allow for the accurate measuring of corrosive elements in the environment.

Numerous methods have been developed over the years to provide a measure of the degradation of materials in industrial applications. Direct methods for assessing degradation of materials can be classified into two categories that include intrusive and non-intrusive techniques. One intrusive technique is the use of test specimens exposed to the environment of interest. Coupons, or representative samples of materials such as metals or plastics, are one of the most typical test specimens used for evaluating degradation. Coupons are one of the oldest and simplest devices for monitoring degradation, and many standards have been developed for specific applications.

Coupons are fabricated in many forms, depending on the application of interest, and the types include rectangular, disk, cylindrical, and u-bend. Best practices for coupon exposure require the use of a test rack, which generally consists of a support structure that attaches the rack to a component in the system and fasteners that hold the coupons to the support. The purpose of the rack is to reproducibly suspend the coupons in the environment at the location of interest and with a proper orientation. A number of requirements need to be met by a suitable rack, including: sufficient sturdiness to support the coupon specimens, resistant construction materials to the environment, suitable exposure of the coupons to the process environment, electrical isolation of the metal coupons from one another and the rack (to prevent galvanic interaction), and prevention of interaction of degradation products from one coupon to another. Common coupon racks that have been used for industrial applications include the flat bar rack, the spool rack, the insert rack for pipelines, and "slip-in" or retractable holders. The current invention is inventive in that it contains a square support beam, which allows for orthogonal mounting of coupons.

The current invention was developed for mounting corrosion coupons in atmospheric environments. Standard atmospheric corrosion tests using coupons generally use flat panel coupons. The most widely used panel specimens for atmospheric corrosion testing are 4 inches by 6 inches (~100 mm by 150 mm) in size. In most atmospheric degradation corrosion, numerous panels are secured using insulating knobs on a large, sturdy frame. However, many industrial applications do not have the available space to install a large frame structure in the environment of interest. The relatively small size of the current invention allows for suspension of numerous corrosion coupons in an environment where available space is an issue. The design of the rack also allows for easy installation to typical equipment in use in industrial settings.

SUMMARY

The current invention describes the following key aspects:
1. It is an advantage of the invention to provide stability in the location of the coupons, at varying orientations and levels.
2. It is an advantage of the invention to require limited space of the use of the invention.
3. It is an advantage of the invention to provide easy installation of the apparatus to industrial equipment.
4. Provides a method for uninterrupted and consistent results.

BRIEF DESCRIPTION OF THE FIGURES

FIG. 3: A top view of the bracket.

DETAILED DESCRIPTION

Figure 1:
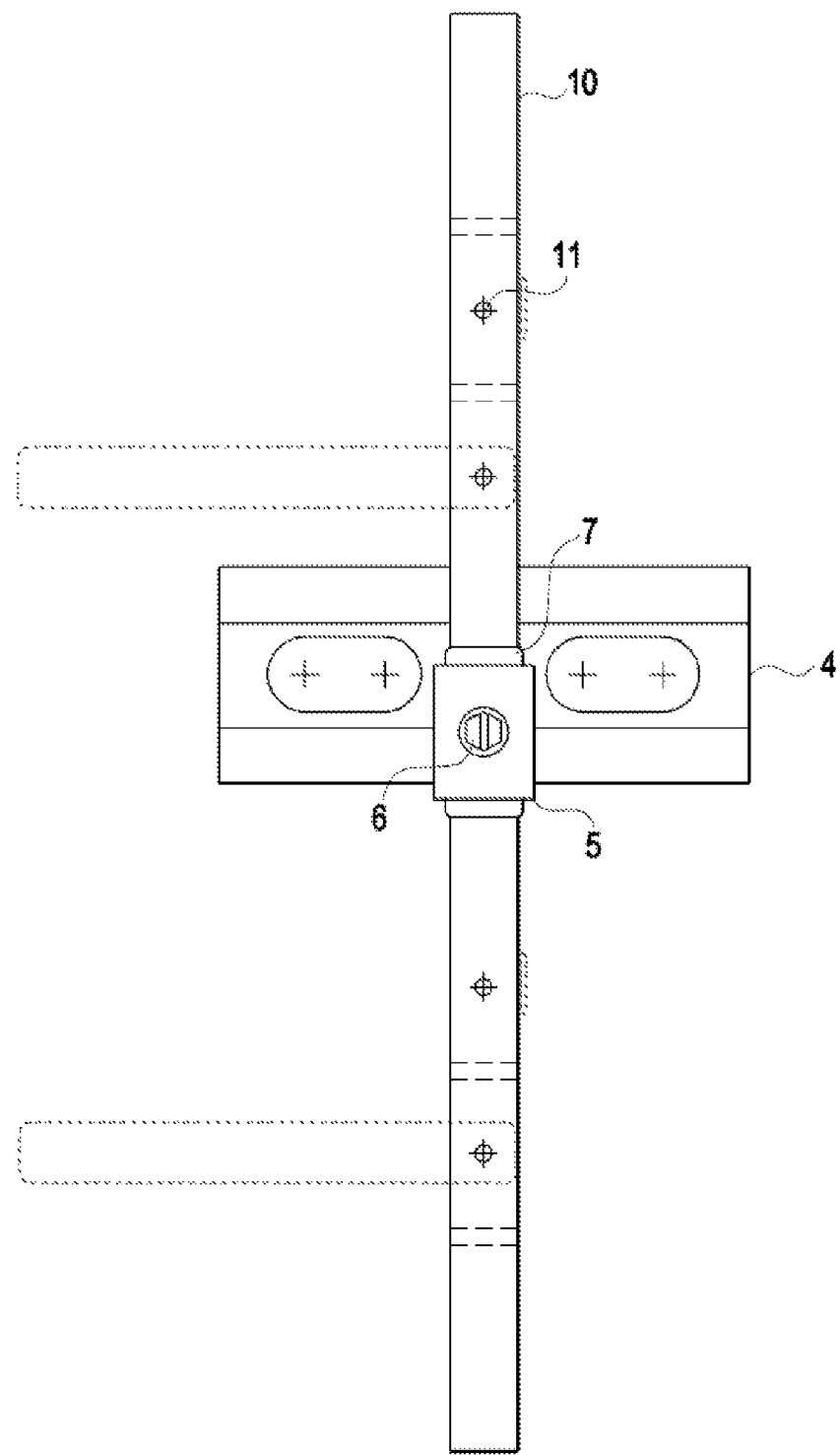
FIG. 1: A front view of the bracket.
Figure 2:
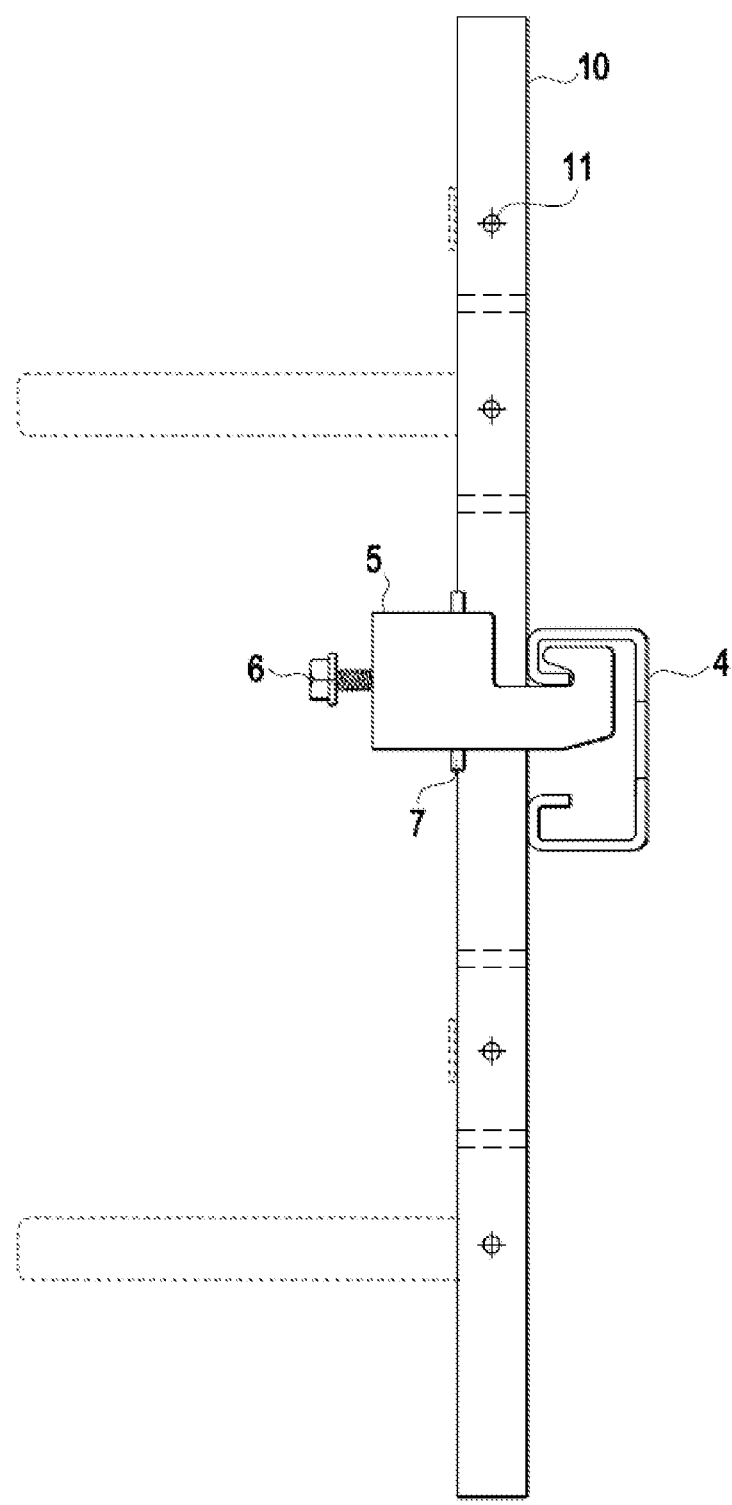
FIG. 2: A side view of the bracket.

The current invention relates to a apparatus for placement of coupons for the testing of an environment on materials using one or more test coupons at a single or varying orientation comprising a bracket attachment member 4, a connection member 5, a bracket adjustment member 6, a bracket stabilizer 7, one or more coupon attachment member(s) 10, and a coupon attachment site 11. The current invention allows for many different bracket attachment members 4 but the preferred is a u-bar. Coupon attachment member 10 contains one or more coupon attachment sites 11. The current invention connects or attaches the coupon attachment member 10 to the bracket attachment member 4 with the connection member 5. The connection member 5 of the current invention is adjustable allowing for the movement of the apparatus to fit multiple locations. The apparatus further has a coupon attachment member 10 has one or more coupon attachment sites 11.

The current invention has a preferred embodiment wherein the coupon attachment member 10 is square allowing for the placement of the coupons in an orthogonal pattern. This square support beam or coupon attachment member allows for orthogonal mounting of coupons. The relatively small size of the current invention allows for suspension of numerous corrosion coupons in an environment where available space is an issue in the environment at the location of interest and with a proper orientation.

The invention further includes a method for sampling effects of degradation on materials in a manufacturing facility where in the apparatus is placed in a facility with one or more coupons attached to the coupon attachment sites 11, the coupons are allowed to react with the environment and facilitate collecting samples for a predetermined period then replaced with new coupons. The invention is used with coupons that are meant to measure degradation elements from vaporous exposure. The method further allows for the use of multiple testing coupons attached to the coupon attachment member 10.

The testing coupons are placed on the coupon attachment member 10 at different levels and angles allowing for the complete testing of the environment. Once the set period of time for testing is complete the coupons are removed and replace with new ones in the same location allowing for long term testing. The method uses a coupon attachment member 10 is a square bar allowing for the placement of multiple coupons in an orthogonal pattern.

It should be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

We claim:

1. An apparatus for placement of coupons for the evaluation of an environment on materials using test coupons at a single or varying orientation comprising:
   (a) a bracket attachment member and a bracket adjustment member,
   (b) a coupon attachment member,
   (c) a connection member which adjustably connects the bracket attachment member to the coupon attachment member,
   (d) a bracket stabilizer disposed on the coupon attachment member and connected to the bracket adjustment member,
   (e) coupon attachment sites disposed along a length of the coupon attachment member, and
   (f) test coupons suspended on the coupon attachment sites and exposed to the environment, wherein the test coupons are attached in an orthogonal pattern to the coupon attachment sites and oriented at a substantially perpendicular angle relative to the coupon attachment member.

2. The apparatus of claim 1 wherein the bracket attachment member is a u-bar.

3. The apparatus of claim 1 wherein the connection member is adjustable.

4. The apparatus of claim 1 wherein the coupon attachment member is square.

5. A method for sampling effects of degradation on materials in a manufacturing facility wherein the apparatus of claim 1 is placed in a facility and the at least one test coupon is allowed react with the environment and facilitate collecting samples after a predetermined exposure period then replaced with new test coupons.

6. The method of claim 5 wherein the at least one test coupon measures degradation elements from vaporous exposure.

7. The method of claim 5 wherein there are multiple testing coupons.

8. The method of claim 7 wherein the multiple testing coupons are placed at different levels and angles.

9. The method of claim 5 wherein the coupons are collected after a set period and new coupons are placed in a same location for long term testing.

10. The method of claim 5 wherein the coupon attachment member is a square bar.

11. The method of claim 10 wherein the square bar allows for the placement of multiple coupons in an orthogonal pattern.

* * * * *